United States Patent [19]

Gibson et al.

[11] Patent Number: 5,928,706

[45] Date of Patent: Jul. 27, 1999

[54] HEAT-STABLE PROTEIN MICROPARTICLES AND NO-SHEAR PROCESS FOR PRODUCING SAME

[76] Inventors: Suzanne M. Gibson, 213 Runyon Ave.; George Strauss, 514 Runyon Ave., both of Piscataway, N.J. 08854

[21] Appl. No.: 08/907,208

[22] Filed: Aug. 6, 1997

Related U.S. Application Data

[60] Provisional application No. 60/023,647, Aug. 9, 1996.

[51] Int. Cl.$^6$ .......................................................... A23J 1/00
[52] U.S. Cl. ........................... 426/656; 426/576; 426/577; 426/658; 426/662; 424/489
[58] Field of Search ...................................... 426/656, 804, 426/99, 662, 577, 98, 658, 576; 424/489, 450

[56] References Cited

U.S. PATENT DOCUMENTS

| | | |
|---|---|---|
| 3,558,323 | 1/1971 | Cannalonga et al. . |
| 4,308,294 | 12/1981 | Rispoli et al. . |
| 4,528,204 | 7/1985 | Shank . |
| 4,734,287 | 3/1988 | Singer et al. . |
| 4,961,953 | 10/1990 | Singer et al. . |
| 5,021,248 | 6/1991 | Stark et al. . |
| 5,139,811 | 8/1992 | Singer et al. . |
| 5,147,677 | 9/1992 | Ziegler . |
| 5,324,531 | 6/1994 | Hoefler et al. . |
| 5,330,778 | 7/1994 | Stark et al. . |
| 5,356,644 | 10/1994 | Hendrick et al. ........................ 426/99 |
| 5,374,441 | 12/1994 | Gibson et al. . |
| 5,413,804 | 5/1995 | Rhodes ................................... 426/656 |
| 5,589,215 | 12/1996 | Tang ....................................... 426/549 |

*Primary Examiner*—Lien Tran
*Attorney, Agent, or Firm*—Mathews, Collins, Shepherd & Gould, P.A.

[57] ABSTRACT

Fat-like protein compositions for use in foods and cosmetics comprising a protein of gelatin and a water-soluble albumin, a carbohydrate, and a phospholipid wherein said gelatin, albumin, carbohydrate, and phospholipids are in the form of a water-insoluble complex coacervate, and processes for making the same. Preferred are compositions wherein some or all of the ingredients are optionally crosslinked.

10 Claims, 1 Drawing Sheet

ILLUSTRATIVE PROCESS FOR PREPARATION OF MICROPARTICLES

HEAT-STABLE PROTEIN MICROPARTICLES AND NO-SHEAR PROCESS FOR PRODUCING SAME

CROSS REFERENCE TO RELATED APPLICATION

This application claims the benefit of U.S. Provisional Application No. 60/023,647 entitled "Heat-Stable Protein Microparticles and No-Shear Process for Producing Same", filed by applicants on Aug. 9, 1996.

BACKGROUND OF THE INVENTION

The invention relates to fat-like protein compositions for use in foods and cosmetics. The food art is continuously searching for improved fat substitutes which retain the texture, taste and appearance of fatty substances, and which can be used in a variety of food products. While the art has developed a number of products which have attempted to solve this problem, these products are often either poor fat substitutes, impractical to produce, or both. Moreover, products containing fats and oils often have a short shelf life.

In the cosmetic art, there is a need for improved substances capable of complexing with numerous cosmetic substances to extend shelf life, and enhance stability and delivery of these substances.

Various types of protein compositions and processes for their formation have been described in the patent literature. U.S. Pat. Nos. 5,021,248 and 5,145,702 (to Stark and Gross) describe water-insoluble proteins (prolamines) which are denatured and precipitated from alcoholic solutions, and then dispersed under shear as microparticles. However, a special apparatus providing for controlled feed of reactants and for dispersion by rapid stirring is required for this process. These products are stable only up to 70° C. (158° F.), making them unsuitable as a fat replacement for baking or similar purposes.

U.S. Pat. Nos. 4,855,156 and 4,961,953 (to Singer), and U.S. Pat. No. 5,147,677 (Ziegler), U.S. Pat. No. 5,173,322 (Melachouris), EP/0345226 (to Habib), EP/0340035 (to Chen), and WO90/05460 (to Liao) describe precipitation by heat-denaturation and microparticulation by shear (in a special apparatus) of water-soluble proteins such as egg white, casein, whey protein and cereal proteins, with addition, in some instances, of lecithin, polysaccharides, and other substances.

U.S. Pat. No. 5,374,441 to Gibson et al. describes precipitation and microparticulation of water-soluble proteins by heat-denaturation under shear, combined with a crosslinking reaction using phenolic acids and an oxidizing agent. The microparticles produced by this process are stable at temperatures of 350–400° F. when used for baking. This product, while having certain desirable properties, is difficult to manufacture on a large scale because it requires an injection step and high-shear agitation.

U.S. Pat. No. 4,734,287 to Singer, et al. describes protein product bases produced by subjecting sweet whey to high shear while simultaneously heating the whey to produce the proteinaceous microparticles.

U.S. Pat. No. 4,308,294 issued Dec. 29, 1981 to Rispoli et al. describes oil replacement compositions prepared by formation of a protein phase, forming a separate acid modified starch phase, heating the acid starch phase to swell the starch, followed by cooling and mixing the protein and acid phases.

SUMMARY OF THE INVENTION

The invention relates to fat-like protein compositions for use in foods, cosmetics, pharmaceuticals, and the like. The compositions comprise water-insoluble microparticle compositions comprising protein, carbohydrate, and phospholipid stabilized by cross-linking them with naturally occurring phenolic acids. The protein portion comprises gelatin and optionally a water-soluble heat-denaturable albumin. The carbohydrates comprise at least one polysaccharide having ionizable groups, and the phospholipids comprise a mixture of charged and uncharged phospholipids. These microparticles can function as a fat replacement in foods, cosmetics or pharmaceuticals. They can also serve to form complexes with a variety of oils or other lipids. The invention also relates to methods for making these compositions. Complex coacervates in the form of water-insoluble microparticles are generated when solutions of gelatin, an albumin, and a polysaccharide are mixed at between about 40° C. and about 45° C., and then acidified. This temperature is important because in order to blend the two proteins, the temperature must ordinarily be above the 37° C. melting temperature of the gelatin but below the temperature range where albumins denature (45–60° C.). The gelatins include acid-processed and alkali-processed gelatins. The albumins include, but are not limited to, egg white, casein, and soy protein. The polysaccharides include, but are not limited to, pectin, carrageenan, alginate, and carboxymethyl cellulose. A variety of art-known albumins and polysaccharides are suitable for use in the instant invention.

As used herein, the term "complex coacervation" is understood to mean the aggregation of colloidal polyelectrolytes from solution when they have acquired opposite net ionic charges, brought about by an appropriate pH change. In contrast to other processes that generate microparticles by heat-denaturation, the present process uses coacervation without any denaturation by heat. The gelatin component, in fact, cannot be denatured this way. The particle size, yield, and rigidity of the coacervates is affected by the concentrations and pH levels used. It is understood that those skilled in the art can modify the pH and concentrations according to their specific needs.

The present process provides for optional subsequent heat treatment, but this step is not an essential part of this invention. Coacervates are more easily generated in high yields when the gelatin solution is first blended with the albumin solution and the phospholipid solution prior to mixing with the polysaccharide solution and acidification. Further, it has been found that the resulting coacervates can be stabilized by adding a phenolic acid, and allowing a crosslinking reaction of such acids with the proteins in the microparticles to proceed under oxidizing conditions. Phenolic acids are understood to include hydroxylated and/or alkoxylated cinnamic and benzoic acids. Such substituted cinnamic acids include, for example, caffeic, ferulic, coumaric, and chlorogenic acids. Such substituted benzoic acids include, for example, vanillic, syringic, ellagic, and gallic acids. Also included are glycosidic derivatives of all such acids and their esters. Additionally, it has been found that the phenolic acids need not be added as the purified compounds but can be added in the form of a natural extract of potato, coffee (green or roasted), tea, grapes, plums, or other fruit, all of which are rich sources of the above phenolic acids. It has also been discovered that the crosslinking reaction occurs under the combined effects of alkaline pH and exposure to atmospheric oxygen, thus eliminating the need of an added oxidizing agent. While other crosslinking agents (such as formaldehyde and gluteraldehyde) are suitable for use in the instant invention, phenolic crosslinking is the preferred method for use in food or health products.

As noted above, the crosslinked coacervates can optionally be further stabilized by briefly heating the aqueous suspension of microparticles to boiling. This step can be performed before or after the crosslinking step. The final suspension can then be concentrated by centrifugation or filtration, and washed free of uncoacervated material by washing.

This basic process can be modified in several ways. The size of the microparticles can be controlled between about 0.1 up to several hundred micrometers by varying the pH levels and concentration during the coacervation step. Removal of uncoacervated material is optional. The degree of crosslinking can be controlled by varying the amount of phenolic acid introduced by the natural extract, and by varying the time and temperature of incubation of the alkaline solution.

The resulting product is a concentrated suspension of microparticles, having a semi-solid consistency. It can be used as replacement, with only one-half the calorific value, of some or all the fat normally present in foods, including foods baked at temperatures at or about 400° F. The product has a smooth mouth feel. When used in baking muffins, in place of a standard shortening, the resulting food is quite similar in appearance, fluffiness, and taste from a control preparation made with butter. Fluffiness can, in some cases, be even superior to a product made with butter.

This product is substantially free of oxidizable lipids. Therefore, foods made with the product are far less susceptible to becoming rancid over time compared to foods containing fats or oils. Consumables made with the present compositions will therefore have a greatly extended shelf-life.

The product can also be used to replace oils in pharmaceutical and cosmetic creams and emulsions. Due to its gelatin and lecithin content, the product retains moisture, and thus can serve as a humectant in cosmetic and pharmaceutical applications.

DETAILED DESCRIPTION OF THE INVENTION

Figure 1:
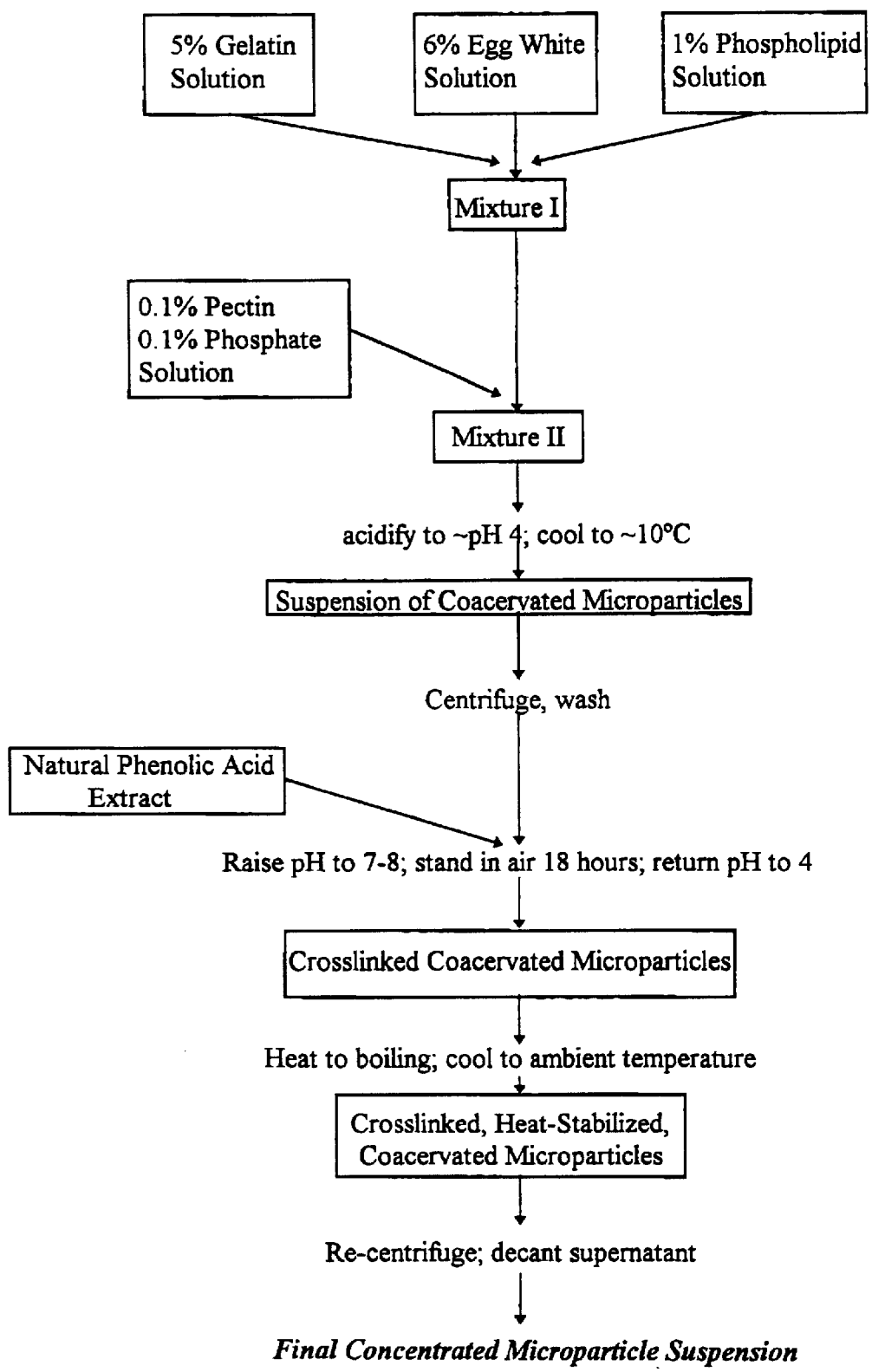
FIG. 1 is a diagrammatic flow chart of a preferred process for preparation of the coacervated microparticles.

The invention thus relates to microparticle protein compositions comprising, (i) a crosslinked protein comprising gelatin and a water-soluble, heat-denaturable albumin, (ii) a carbohydrate comprising at least one polysaccharide having ionizable groups, and (iii) a phospholipid comprising a mixture of charged and uncharged phospholipids; wherein said gelatin, albumin, carbohydrates, and phospholipids are in the form of a water-insoluble complex coacervate.

The resulting microparticles are preferably in the range of from about 0.1 to about 250 microns. More preferred are microparticles in the range of from about 0.1 to about 10 micrometers, and microparticles in the range of from about 10 microns to about 250 microns.

The albumin is preferably egg white or lactalbumin. The preferred carbohydrate is pectin or carboxymethyl cellulose.

The invention also relates to processes for producing fat-like protein compositions using suitable amounts of gelatin, albumin, carbohydrate, and phospholipid. These elements may be dissolved separately in water at a pH between about 4.5 and about 9.0. Next, the gelatin, albumin, carbohydrate, and phospholipid are combined to form a mixture. The mixture is then acidified to a pH of between about 4.4 and about 3.8 to produce a precipitate of coacervated microparticles. An effective amount of phenolic acid or derivative thereof is then added to the suspension of microparticles; and the pH of the suspension is raised to a pH of between about 7 and about 9. The suspension can be contacted with air for a suitable period of time if desired. The suspension is then acidified to a pH between about 4 and about 5, heated until boiling, then allowed to cool to room temperature.

The suspension can optionally be concentrated by centrifugation or filtration. Additionally, the suspension can be optionally washed with an alcohol, and the suspension allowed to dry to a powder, capable of reconstitution to the original fat-like suspension through rehydration with water.

The preferred phenolic acids in the invention are chlorogenic acid, caffeic acid, ferulic acid, coumaric acid, other suitable members of this class of acids, and mixtures and derivatives thereof.

A preferred procedure for forming the protein microparticles, is as follows:

1. A 5% solution of gelatin is made by allowing the gelatin to hydrate at room temperature, then warming it to 40° C. The pH is adjusted to 4.8 by addition of acetic acid or sodium hydroxide. Acid-type or alkali-type gelatins of bloom strengths up to 300 can be used, depending on the desired texture of the microparticles.

2. A 6% solution of egg white (egg albumin) is made by slowly adding dried egg white to water at room temperature while stirring, and continuing stirring for one hour. Centrifugation at 2000 rpm for 5 minutes is used to remove undissolved material. Before use the solution is warmed to 40° C. Other albumins such as milk or soybean proteins can also be used.

3. A 1% suspension of phospholipids is prepared by stirring a phospholipid fraction containing at least 50% lecithin (phosphatidyl choline) into water at 40° C. Phospholipids from egg yolk or soybeans can be used.

4. A solution containing 0.1% of sodium hexametaphosphate and 0.1% of pectin is prepared by adding these solutes to water at 40° C. and slowly adding a 1 Normal sodium hydroxide solution to bring the pH to 8. The solution is stirred for about one hour until the pectin is dissolved. Acetic acid or vinegar is now added to bring the pH to 4.8. Pectins from apples or citrus fruit are suitable. Other polysaccharides with ionizable groups, such as carboxymethylcellulose, can also be used. A pectin:gelatin weight ratio higher than given here can be employed. This ratio affects the yield, and particle size of the microparticles.

5. Four parts of the 6% egg white solution is slowly poured into 36 parts of the 5% gelatin solution at 40° C. and gently blended by stirring for 15 minutes. Six parts of the 1% phospholipid suspension is added and stirring is continued for 10 minutes. This mixture is poured into 54 parts of the sodium hexametaphosphate-pectin solution with stirring which is continued for another 10 minutes, maintaining the temperature at 40° C.

6. Vinegar or 1% acetic acid is slowly added with stirring. As the pH is lowered a precipitate of coacervated microparticles gradually forms. Acidification is continued to a pH of 4.3. Under these conditions, particles of 1–3 micrometers result. Stirring is continued for a further 15 minutes. At this point the reaction mixture contains about 2% of suspended particles plus solutes. The particle size can be controlled by varying the pH values before and after mixing. Larger particles (up to several hundred micrometers) result when the gelatin-albumin solution and the pectin solution are above pH 4.8, possibly as high as 9, before mixing and if acidification after mixing is carried to a point below pH 4.3, possibly as low as 3.5. Smaller particles (between about 1 and 10 micrometers) result when the solutions are below pH 4.8 before mixing, in which case coacervation and precipitation can occur even before further acidification after mixing, and if such acidification stops at a point above 4.3.

7. The suspension is filtered or centrifuged to concentrate it and to remove most of the supernatant solution containing uncoacervated material. Remaining uncoacervated material is removed by washing of the filter cake or by re-centrifugation. Removal of uncoacervated material can be omitted. In this case the final product will be a much thicker suspension, with excellent mouth feel.

8. The proteins in the concentrated particle suspension are then subjected to a crosslinking reaction by adding the juice from raw potato pulp. Peeled potato pulp at 10° C. is passed through a juicer. 12% acetic acid is added immediately, bringing the pH to 4.9. The juice is kept cold and filtered through a paper filter, then added to the concentrated particle suspension that had been precooled to 10° C. The potato juice was analyzed by UV absorption at 280 and 320 nm relative to a standard, and found to contain 150 micrograms of phenolic acids, expressed as chlorogenic acid, per ml of juice. Enough potato juice is added to provide 1.0 to 1.2 milligrams of chlorogenic acid per gram of gelatin present. The pH of the suspension next is raised to 8 or 9 by addition of sodium hydroxide with rapid stirring, then kept at 10–15° C. with slow stirring in an open vessel exposed to air for a minimum of 4 hours. Less alkaline conditions, such as pH 7.5 can be used, with air exposure for 12 to 18 hours. The pH is then readjusted to 4 by adding acetic acid.

9. Optionally the particle suspension at pH 4 can be heated to boiling, then cooled back to room temperature. This step can be omitted where heat-stability of the final product is not required. In this case the final product will have a thinner consistency.

10. Sodium benzoate is added in a concentration of 0.01% to the coacervated, crosslinked, and heat-denatured particle suspension which is then concentrated by filtration or centrifugation. Typically, a suspension containing 40–45% by weight of particles can be prepared which is a semi-solid, smooth, fat-like material.

This procedure can be described by the flow chart in FIG. 1.

The crosslinked microparticles can optionally be washed with 70% isopropanol and evaporated to dryness. The resulting powder can be rehydrated by adding water and vortexing. The microparticles retain their original size and shape. Additives such as glycerine can be added to aid in the rehydration.

It has been found that the microparticles are capable of complexing with water insoluble substances. For example 0.25% powdered beta-carotene was mixed into the 1% phospholipid suspension at 40° C., and the 5% gelatin and the 6% egg white solutions were warmed to 40° C. and added. This mixture was poured into the 0.1% phosphate-pectin solution, as in the above procedure. This technique provides for administration of a water-insoluble substance in an aqueous medium.

The protein microparticles can also be complexed with an oil. Typically a 3% emulsion of vegetable oil is prepared with rapid stirring into a 40° C., 18% gelatin solution until the oil droplets are of the desired size (usually less than 5 micrometers). The high gelatin concentration is needed to aid in the emulsification of the oil. A 40° C., 6% solution of egg albumin is then stirred in. The gelatin/oil/egg albumin mixture is then poured into a solution containing 0.1% sodium hexametaphosphate and 0.1% pectin at 40° C. The pH is then lowered with acetic acid to around 4.0, resulting in the formation of microparticles complexed with small oil droplets. These microparticle complexes are then crosslinked and concentrated as above.

The following examples will serve to further typify the nature of the invention, but should not be construed as a limitation on the scope thereof.

EXAMPLE 1

Solutions were prepared in beakers of appropriate size, equipped with motorized stirrers, and set on thermostatically controlled hotplates.

Solution 1: 50 grams of acid-type gelatin of 300 bloom strength was added with stirring to 1000 ml water at room temperature. This was allowed to hydrate for 30 minutes, and then warmed to 40° C. The pH was adjusted to 4.8 by addition of a small amount of 1 Normal NaOH.

Solution 2: 7.5 grams of dried egg white was slowly stirred into 125 ml water. Stirring was continued for one hour. The solution was centrifuged in a bench centrifuged to remove traces of insoluble material (2000 rpm for about 5 minutes). The clear supernatant was decanted and warmed to 40° C.

Solution 3: 1.7 grams of soybean phospholipids was stirred into 175 ml water at 40° C., producing a colloidal solution.

Solution 4: 1.5 grams of sodium hexametaphosphate and 1.5 grams of citrus pectin were added to 1500 ml water at 40° C. The pH was brought to 8 through addition of 1 Normal NaOH, and the solution was stirred to dissolve the pectin (about an hour). The pH was then brought to 4.8 through addition of 12% acetic acid.

The 125 ml egg white solution was slowly poured with stirring into the 1000 ml of gelatin solution, and stirring was continued for 15 minutes. The 175 ml of phospholipids was added next and stirring was continued for 10 minutes. The resulting 1300 ml of mixture was then slowly poured with stirring into the 1500 ml of phosphate-pectin solution, and stirring continued for 10 minutes.

The pH was then brought to 4.3 through addition of 12% Acetic acid in small aliquots with continuous measurement of the pH. Increasing precipitation occurred during this addition, indicating the formation of an insoluble gelatin-pectin-egg white coacervate. Examination of the precipitate under the microscope showed it to consist of spherical particles of 2 to 3 micrometer in diameter.

The suspension was centrifuged in a bench centrifuge at 2000 rpm for 15 minutes. The microparticles were readily thrown down. They were freed of uncoacervated material by decanting the supernatant, adding fresh water and recentrifuging.

An extract of peeled raw potato was prepared by passing 600 grams of cold (10° C.) potato pulp through a juicer. 400 ml of juice were obtained. The pH was then brought pH to 4.9 through immediate addition of 12% acetic acid. Low temperature and acidification without delay is necessary since the freed phenolic acids otherwise would oxidize and polymerize, with darkening, in the absence of protein. The juice was clarified by passing it through a paper filter, and added to the washed suspension of microparticles. The 400 ml of potato extract provided 60 milligrams of chlorogenic acid (caffeoylquinic acid) for reaction with 50 grams of gelatin. The suspension was adjusted to pH 7.5 by addition of 0.12% NaOH, and kept in an open beaker at 10° C. to 15° C. with slow stirring for 18 hours. The pH was then lowered to 4 by addition of acetic acid.

The particle suspension next was heated to boiling, then cooled back to room temperature. Microscopic examination showed no change in size or shape of the microparticles after this treatment. After this treatment, the suspension became whiter in appearance and more viscous.

Sodium benzoate (0.1 gram per liter of suspension) was added as a preservative. The suspension was centrifuged again to concentrate it. After decanting the supernatant, the concentrated residue amounted to 135 grams, with a solids content of 45%.

EXAMPLE 2

Retention of Uncoacervated Material

The procedure of Example 1 was repeated but the removal of uncoacervated material was omitted. The final product, containing the ingredients both in the coacervated and in the free state, had a much thicker consistency than the product of Example 1.

EXAMPLE 3

Crosslinking with Grape Juice

Commercial grape juice was analyzed and found to contain 300 micrograms of phenolic acids per ml. The procedure of Example 1 was used but the potato extract was replaced with grape juice in an amount sufficient to provide 3.5 milligrams of phenolic acids per gram of gelatin present. After addition of the grape juice to the particle suspension at pH 4, the mixture was brought to pH 9 and kept stirred and exposed to air for two hours at 15° C. The solution was then returned to pH 4, and further treated as in Example 1.

EXAMPLE 4

Crosslinking with Coffee

Instant coffee (which was found to contain 100 milligrams of chlorogenic acid per gram of coffee powder) was dissolved in hot water and enough coffee extract was added to the microparticle suspension to provide 5 milligrams of chlorogenic acid per gram of gelatin present. The mixture was brought to pH 7.5 and kept exposed to air for 18 hours.

EXAMPLE 5

Microparticles as Fat Replacement in Baking

Microparticles were prepared without washing as set forth in Example 2, then crosslinked with coffee as in Example 4. Muffins were baked, using these microparticles in the following recipe:

1) 1 cup flour, ½ teaspoon salt, 2 tablespoons sugar, and 1 teaspoon baking powder were mixed together.

2) In a second bowl, 1 egg, ½ cup milk, and 2 tablespoons of crosslinked microparticles were mixed together.

This wet mixture was poured into the dry ingredients and stirred just until there were no large lumps. The batter was poured into paper baking cups placed in a muffin tin. The muffins were baked in a 400° F. oven for 20 minutes. The muffins were similar in appearance, fluffiness, and taste from muffins made in the same way, using butter instead of the microparticles.

EXAMPLE 6

Complexation of Microparticles with a Water Insoluble Compound

The quantities of Example 1 were used. One-half gram of beta-carotene (from Sigma Chemical Co.) was added with stirring to the phospholipid solution. The phospholipid solution was then added to the egg white and gelatin solutions. The phospholipid was found to aid in dispersion of the crystalline carotene. The mixed solution was then poured into the phosphate-pectin solution, and the procedure was continued as in Example 1. When the final microparticle suspension was washed with water and diluted, the carotene remained associated with the microparticles, as indicated by its the strong red color.

EXAMPLE 7

Complexation of Microparticles with an Oil

1. A gelatin solution was prepared by dissolving 5.4 g of 300 Bloom gelatin in 25.1 g of water.

2. 0.7 g of egg albumin was dissolved in 11.8 g of water.

3. 1 ml of vegetable oil was emulsified into the warm gelatin until small droplets (less than 5 $\mu$m were formed.

4. The centrifuged egg albumin was warmed to 40° C. and gently stirred into the gelatin/oil mixture.

5. To 150 ml 40° C. water, 0.1 ml of 2N NaOH, 0.2 g sodium hexametaphosphate and 0.2 g pectin was added. When the pectin was dissolved, pH was adjusted to 4.81 with the addition of 0.2 ml of 12% acetic acid.

6. The warm gelatin/egg/oil mixture was poured into the pectin solution with stirring. The pH of mixing was 4.66. 3 ml of acetic acid was added to a final coacervation of 4.04.

7. Microscopic examination confirmed the formation of gelatin/egg albumin microparticles approximately 15–20 microns in diameter. These microparticles were complexed with several tiny oil droplets.

8. The protein microparticles were crosslinked with 60 ml grape juice as in Example 3.

What is claimed:

1. A protein composition comprising water-insoluble coacervate microparticles, said coacervate microparticles comprising:

a) a protein comprising gelatin and a water-soluble albumin;

b) a carbohydrate comprising at least one polysaccharide having ionizable groups, and c) a phospholipid comprising a mixture of charged and uncharged phospholipids, wherein the coacervated microparticles are crosslinked by a phenolic acid.

2. The composition according to claim 1 wherein the phenolic acid is obtainable from a fruit or vegetable source.

3. The composition according to claim 1 wherein the microparticles are in a size range of from about 0.1 to about 10 micrometers.

4. The composition according to claim 1 wherein the microparticles are from about 10 to about 250 micrometers.

5. The composition according to claim 1 wherein the microparticles are stable at temperatures up to 400° F.

6. The composition according to claim 1 wherein said gelatin is an acid-type gelatin with bloom strengths of about 300 or less.

7. The composition according to claim 1 wherein the albumin is selected from the group consisting of egg white and lactalbumin.

8. The composition according to claim 1 wherein the carbohydrate is pectin.

9. The composition according to claim 1 wherein the carbohydrate is carboxymethyl cellulose.

10. The composition according to claim 1 wherein a water-insoluble substance is incorporated within the microparticles, wherein said water-insoluble substance is oil.

* * * * *